United States Patent
Downey

(10) Patent No.: US 7,630,080 B2
(45) Date of Patent: *Dec. 8, 2009

(54) REFRACTIVE INDEX SENSOR UTILIZING GOLD ISLAND SURFACE PLASMON RESONANCE ON OPTICAL FIBER

(75) Inventor: Todd R. Downey, Monroe, CT (US)

(73) Assignee: ASML Holding N.V., Veldhoven (NL)

( * ) Notice: Subject to any disclaimer, the term of this patent is extended or adjusted under 35 U.S.C. 154(b) by 0 days.

This patent is subject to a terminal disclaimer.

(21) Appl. No.: 12/172,727

(22) Filed: Jul. 14, 2008

(65) Prior Publication Data

US 2009/0015841 A1     Jan. 15, 2009

Related U.S. Application Data

(63) Continuation of application No. 11/834,384, filed on Aug. 6, 2007, now Pat. No. 7,426,034, which is a continuation of application No. 10/953,359, filed on Sep. 30, 2004, now Pat. No. 7,253,888.

(51) Int. Cl.
G01N 21/55 (2006.01)

(52) U.S. Cl. ..................................... 356/445
(58) Field of Classification Search ........................ None
See application file for complete search history.

(56) References Cited

U.S. PATENT DOCUMENTS 5,812,255 A   9/1998   Lau et al.
7,253,888 B2  8/2007   Downey
7,426,034 B2  9/2008   Downey

FOREIGN PATENT DOCUMENTS

JP         11-037922 A    2/1999

(Continued)

OTHER PUBLICATIONS

Downey, T., "Gold-Island Thin Film Surface Plasmon Excitation on an Optical Fiber," in *A Thesis Presented for the Master of Science Degree* The University of Tennessee, Knoxville, pp. 1-104 (May 1998).

(Continued)

*Primary Examiner*—Gregory J Toatley, Jr.
*Assistant Examiner*—Amanda H Merlino
(74) *Attorney, Agent, or Firm*—Sterne, Kessler, Goldstein & Fox P.L.L.C.

(57) ABSTRACT

A system for measuring an index of refraction that has a light emitting diode and a plurality of reference fibers not in contact with a sample to be measured and that receive light from the light emitting diode. A plurality of sensing fibers with different-shaped plasmon sensors are in contact with the sample and receive light from the light emitting diode. Detectors sense an output of the light from the fibers. The sensing fibers can be arrayed in a planar arrangement, or in a bundle. A cylindrical lens can be used for directing light into the fibers. A plurality of light emitting diodes can be used, each directing its light output into a corresponding fiber. A ball lens can be used for directing the light into the reference fiber. A plurality of wavelength filters can be placed between the light emitting diode and the sensing fiber, and a wavelength of the light entering the fiber may be selected using the filters.

15 Claims, 5 Drawing Sheets

FOREIGN PATENT DOCUMENTS

| | | |
|---|---|---|
| JP | 11-160317 A | 6/1999 |
| JP | 2003-262586 A | 9/2003 |
| JP | 2004-245638 A | 9/2004 |

OTHER PUBLICATIONS

Meriaudeau, F., et al., "Multiple gold island layers on a fiber core: a promising sensing device," *Opt. Eng,* 40(5):658-660, Society of Photo-Optical Instrumentation Engineers (2001).

Meriaudeau, F., et al., "Gold island fiber optic sensor for refractive index sensing," *Sensors and Actuators B 69*:51-57, Elsevier Science S.A. (2000).

Orfanides, P. et al., "Demonstration of surface plasmons in metal island films and the effect of the surrounding medium—An undergraduate experiment," *Am. J. Phys. 68*(10):936-942, American Association of Physics Teachers (2000).

Meriaudeau, F. et al., "Fiber optic sensor based on gold island plasmon resonance," *Sensors and Actuators B 54*:106-117, Elsevier Science S.A. (1999).

Meriaudeau, F. et al., "Thin Metal Island Plasmon Sensor," Oak Ridge National Laboratory, pp. 1-6.

Meriaudeau, F. et al., "Development of a Fiber Optic Sensor Based on Gold Island Plasmon Resonance," Oak Ridge National Laboratory, pp. 1-6.

Meriaudeau, F. et al., "Environment effects on surface-plasmon spectra in gold-island films potential for sensing applications," *Applied Optics* (37)34:8030-8037 Optical Society of America (1998).

Translated Office Action, dated Jan. 19, 2007, for JP Patent Application No. 2005-287120, 3 pages.

Liedberg et al., "Surface Plasmon Resonance for Gas Detection and Biosensing", *Sensors and Actuators*, vol. 4, pp. 299-304, 1983.

REFRACTIVE INDEX SENSOR UTILIZING GOLD ISLAND SURFACE PLASMON RESONANCE ON OPTICAL FIBER

CROSS REFERENCE TO RELATED APPLICATION

This application is a continuation of U.S. application Ser. No. 11/834,384, filed Aug. 6, 2007 (now U.S. Pat. No. 7,426,034), which is a continuation of U.S. application Ser. No. 10/953,359, filed Sep. 30, 2004 (now U.S. Pat. No. 7,253,888), both of which are incorporated by reference herein in their entirety.

BACKGROUND OF THE INVENTION

1. Field of the Invention

The present invention is generally related to surface plasmon resonance based devices. More particularly, the present invention is related to surface plasmon resonance devices used in a photolithographic system.

2. Related Art

Surface plasmon resonance (SPR) is the oscillation of the plasma of free electrons that exists at a metal boundary. These oscillations are affected by the refractive index of the material adjacent the metal surface. Surface plasmon resonance may be achieved by using an evanescent wave that is generated when a p-polarized light beam is totally internally reflected at the boundary of a medium, e.g., glass, which has a high dielectric constant. A paper describing the technique has been published under the title "Surface plasmon resonance for gas detection and biosensing" by Lieberg, Nylander and Lundstrom in *Sensors and Actuators*, Vol. 4, page 299 (1983).

FIG. 1A shows a diagram of the conventional plasmon sensor equipment described in the Lieberg paper. An incident beam of light 1 is directed from a laser source (not shown) onto an internal portion of surface 2 of a glass body 3. A detector (not shown) monitors the internally reflected beam 4. Applied to the external portion of surface 2 of glass body 3 is a thin film of metal 5, for example gold or silver, and applied to the film 5 is a further thin film of material 6. A sample 7 is brought into contact with the film 6 to thus cause a reaction. If binding occurs, the refractive index of the film 6 will change, and this change can be detected and measured using surface plasmon resonance techniques.

Surface plasmon resonance can be experimentally observed by varying the angle of the incident beam 1 and monitoring the intensity of the internally reflected beam 4. At a certain angle of incidence, the parallel component of the light momentum will match with the dispersion for surface plasmons at the opposite surface 8 of the metal film 5. Provided that the thickness of metal film 5 is chosen correctly, there will be an electromagnetic coupling between the glass/metal interface at surface 2 and the metal/sample interface at surface 8, resulting in surface plasmon resonance, and thus attenuation in the reflected beam 4 at that particular angle of incidence. Thus, as the angle of incidence of incident beam 1 is varied, surface plasmon resonance is observed as a sharp dip in the intensity of the internally reflected beam 4 at a particular angle of incidence. The angle of incidence at which resonance occurs is affected by the refractive index of the material against the metal film 5, i.e. the film 6, and the angle of incidence corresponding to resonance is thus related to the refractive index of the sample. Increased sensitivity can be obtained by choosing an angle of incidence halfway down the reflectance dip curve where the response is substantially linear, and then maintaining that angle of incidence fixed and observing changes in the intensity of the reflected beam 4 with time. This is illustrated in FIG. 1B.

As the angle of incidence is changed, either by moving the light source or rotating the glass body, or both, the point on surface 2 at which the incident beam 1 is incident moves. Because of inevitable variations in the metal film 5 and the film 6, the angle of incidence at which resonance occurs changes as the point of incidence of incident beam 1 moves, which, in turn, introduces a further variable factor into the measurement and thus makes comparison between the initial unbound state and the bound state of the film 6 less accurate.

Newly developed lithography machines with immersion have a fluid between the last lens of the projection optics (PO) and the wafer. Ultra pure water is used in such immersion lithography machines that utilize excimer lasers (that emit light at a wavelength of, e.g., 193 nm), and flows between the last lens element of the PO and the substrate (e.g., a wafer, a flat panel display, a printhead, or the like) in order to enlarge the depth of focus and to enable POs with a numerical aperture (NA) larger than 1. This enables the critical dimension of the semiconductor devices to be reduced. In order to avoid contamination of the projection optics and wafer, the water must be clean. In order to avoid shading effects during projection, the water needs to be free of particles and bubbles. Particles are also to be avoided to minimize the number of contaminants deposited on the wafer. The supply also needs to maintain a refractive index (n) of the fluid that is within a very small range. However, the refractive index n of the immersion media (IM) can vary due to the introduction of contaminants. Out-of range variations in n will lead to variations in critical dimension and critical dimension uniformity that will reduce wafer yield.

There is a need in the art for an improved SPR sensor, as well as for apparatus and methods relating thereto.

SUMMARY OF THE INVENTION

The present invention is directed to a refractive index sensor utilizing gold island surface plasmon resonance on an optical fiber that substantially obviates one or more of the problems and disadvantages of the related art.

An embodiment of the present invention includes a system for measuring an index of refraction that has a light emitting diode and a reference fiber that is not in contact with a sample to be measured and that receives light from the light emitting diode. A plurality of sensing fibers with different-shaped plasmon sensors are in contact with the sample and receive light from the light emitting diode. Each sensing fiber has a corresponding reference fiber having same plasmon shape, the reference fibers not being in contact with the sample. Detectors sense an output of the light from the fibers. The sensing fibers can be arrayed in a planar arrangement, or arrayed in a bundle. A cylindrical lens can be used for directing light into the fibers. A plurality of light emitting diodes can be used, each directing its light output into a corresponding fiber. Ball lenses can also be used for directing the light into the fibers. A plurality of wavelength filters can be placed between the light emitting diode and the sensing fiber, and a wavelength of the light entering the fiber may be selected using the filters.

Additional features and advantages of the invention will be set forth in the description that follows, and in part will be apparent from the description, or may be learned by practice of the invention. The advantages of the invention will be realized and attained by the structure and particularly pointed out in the written description and claims hereof as well as the appended drawings.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to illustrate exemplary embodiments of the invention and are incorporated in and constitute a part of this specification, illustrate embodiments of the invention and together with the description serve to explain the principles of the invention. In the drawings.

DETAILED DESCRIPTION OF EMBODIMENTS OF THE INVENTION

Reference will now be made in detail to the embodiments of the present invention, examples of which are illustrated in the accompanying drawings.

Figure 1A:
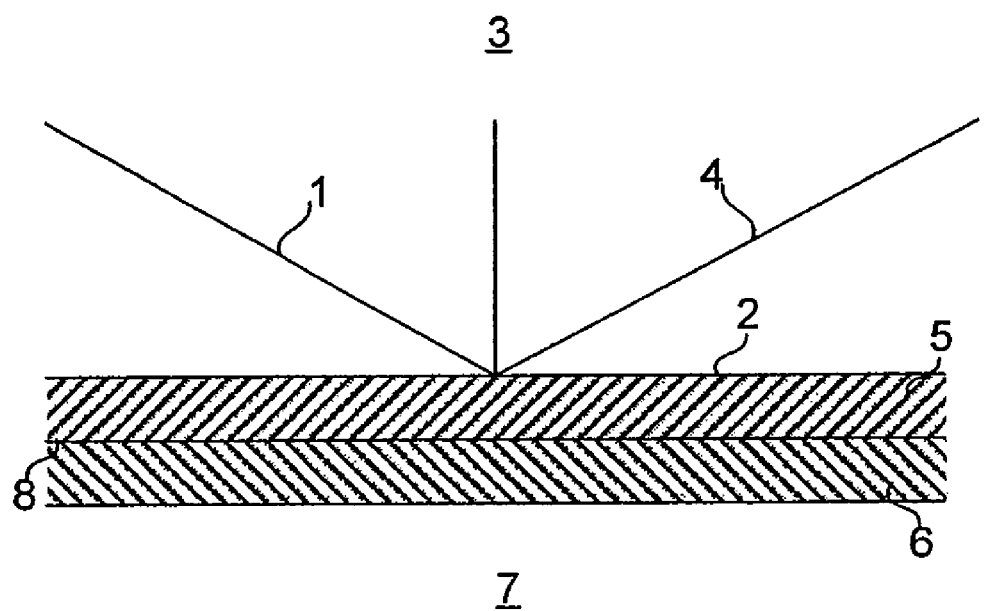
FIG. 1A shows a diagram of conventional plasmon sensor equipment.
Figure 1B:
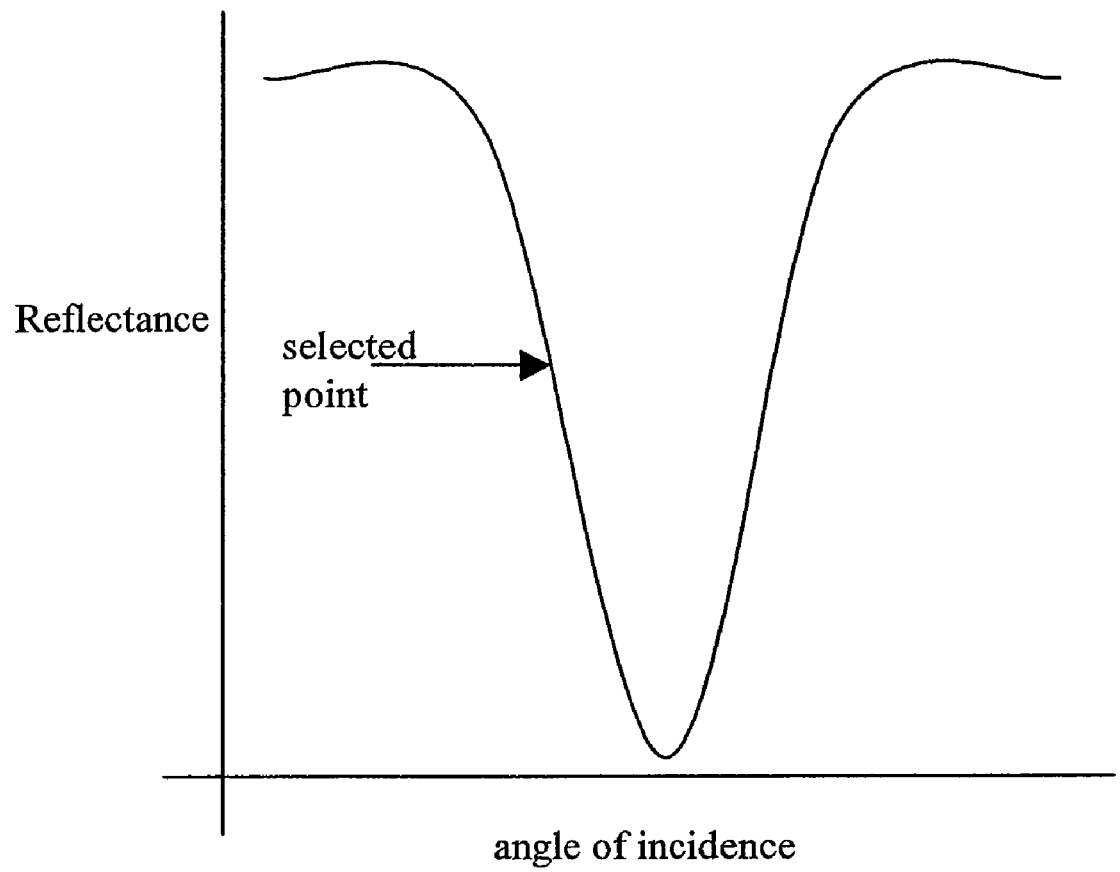
FIG. 1B shows a reflectance curve for a conventional plasmon sensor.
Figure 2:
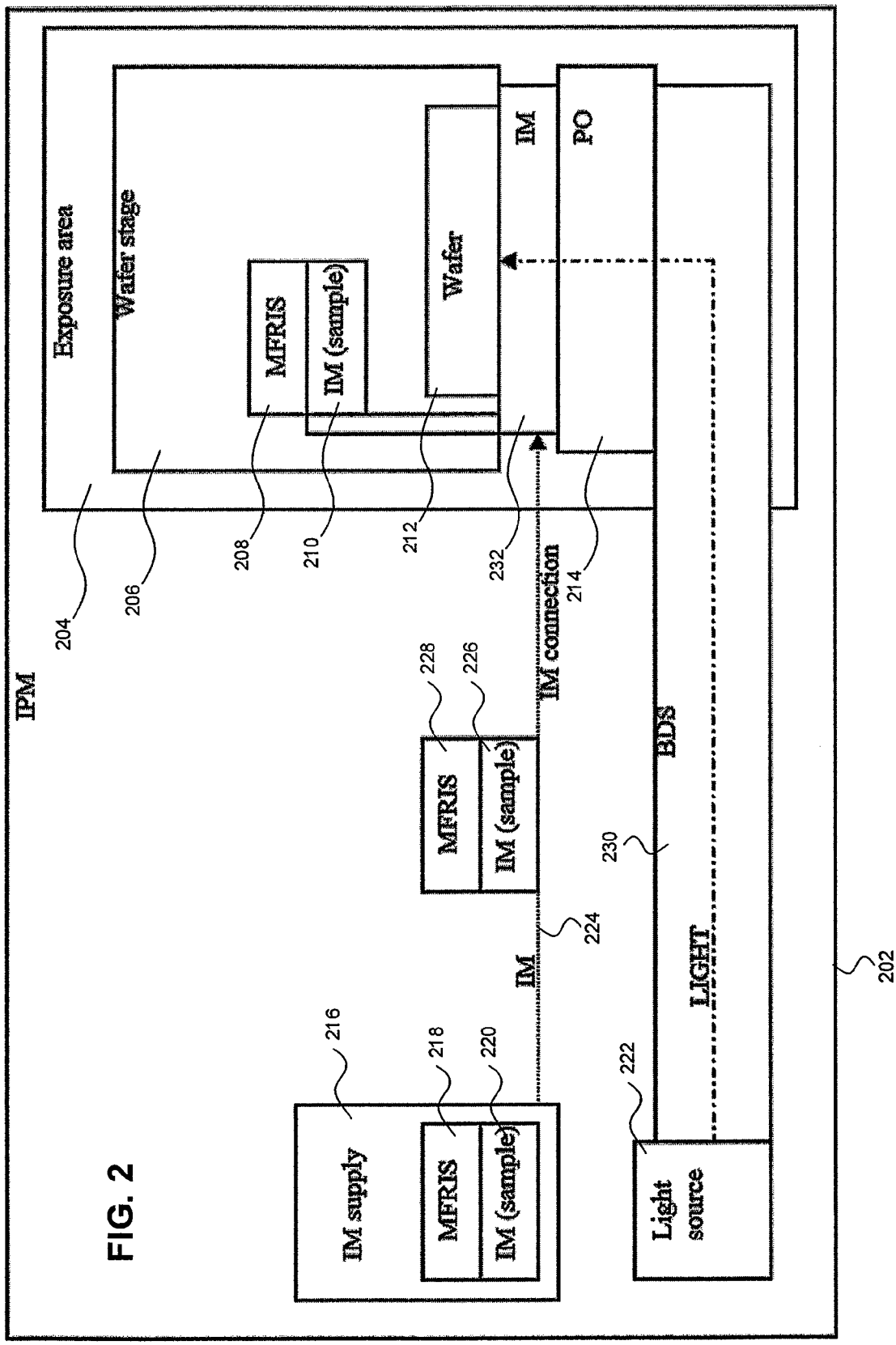
FIG. 2 shows a diagram of a lithographic machine where a plasmon sensor may be used.

FIG. 2 illustrates an exemplary lithographic system that utilizes a sensor according to the present invention. As shown in FIG. 2, an immersion lithography machine 202 includes an exposure area 204, with a wafer stage 206 having a substrate 212 (such as a wafer, or a flat panel display) mounted thereon. Projection optics 214 is used to project light from a light source 222, the light being delivered using a beam delivery system 230. An immersion medium (IM) 232 is located between the projection optics 214 and the wafer 212, and is normally recirculated. An immersion medium supply 216 supplies the immersion medium 232 through an IM connection 224. Sensors ("MFRIS") 218, 228, and 208, which are further described below, may be located at some or all of the positions shown in FIG. 2. For example, the sensor 228 samples an IM sample 226, at the location shown. The sensor 218 samples an immersion medium sample 220, at the location shown. An additional immersion medium sample 210 may be taken at the location shown, for the sensor 208.

Laser light is supplied to the exposure area by the beam delivery system (BDS) 230. The light is sent through the PO 214, the IM 232, and is finally delivered to the wafer 212. Note that the critical exposure area 204 is at the interface of the wafer 212 and the immersion media 232.

The immersion media supply 216 can be inside the immersion lithography machine 202. A surface plasmon sensor 218 can be incorporated in the immersion media supply 216, along an immersion media connection line 224, or on a wafer stage in the exposure area 204. In either case, a small portion of the immersion media 232 to be delivered can be sampled by the surface plasmon sensor (208, 218, 228).

Thus, ultra pure water is supplied to an immersion lithography machine 202 via an internal ultra pure water supply system 216 that is usually a part of the immersion lithography machine 202. It requires a connection to the external ultra pure water supply (not shown in the figure) that is available from the fabrication building that houses the immersion lithography machine 202. The reliance of the ultra pure water supply system on an external source of ultra pure water to condition and monitor the water before delivering it to the exposure area 204 of machine 202 requires a set of sensors in the internal ultra pure water supply 216 to verify index of refraction n. In all such immersion lithography machines 202, the index of refraction n of the immersion media 232 must be verified in-situ, to assure proper wafer yield.

Other liquids or gases can be used for the immersion media. Examples of other immersion media fluids include water with specific salts added to increase n. Fluids can be used in immersion lithography machines that operate with different wavelengths, e.g., 157 nm, 248 nm and 356 nm (either using lasers or using lamp systems forming the light source 222). Gases with large values for n can also be used in immersion lithography machines as the immersion media 232.

Conventional sensors either use a simple fiber, or use the same coatings on the all the sample fibers. The same gold island coating on every fiber leads to the same distribution of island shapes on every fiber. The same distribution of island shapes leads to the resonant absorption peak occurring at the same wavelength of the incident light, and the same red-shift of the peak when a sample liquid or gas is applied the active areas of the fibers.

In the present invention, instead of utilizing M sample fibers that have been prepared together (gold deposition and annealing) in order to form the same gold island coating on every fiber, the proposed surface plasmon sensor has M sample fibers with M different gold island coatings (here, M is an integer).

There are different coatings on at least 2 sample fibers. Also, a preferred embodiment includes M coated reference fibers, each being prepared with their respective coated sample fiber so that the same coating is applied to each. There are M pairs of coated sample and reference fibers, with each pair having the same coating applied to both fibers, but M different coatings are applied to the M pairs. The single uncoated reference is still required. The same measurement procedures apply, including that only the M sample fibers are immersed in the liquid or gas to be measured, not the reference fibers.

Applying a slightly different coating to each of the M fibers will lead to M different wavelengths for the absorption peaks. In order to apply slightly different coatings to M fibers, the annealing temperature needs to be carefully controlled. In general, a lower annealing temperature will form flatter islands and smaller values of R (R=ratio of the prolate spheroid minor and major axis lengths). The objective is to obtain M different wavelengths for the absorption peaks for the M fibers. These M different wavelengths are close enough to each other for all of them to be well within the entire range of wavelengths produced by the LED source and the band-pass filters, but are separated enough to allow for easily discernable position of two adjacent absorption peaks with the limited set of wavelengths produced by the LED source and the band-pass filters.

Figure 3:
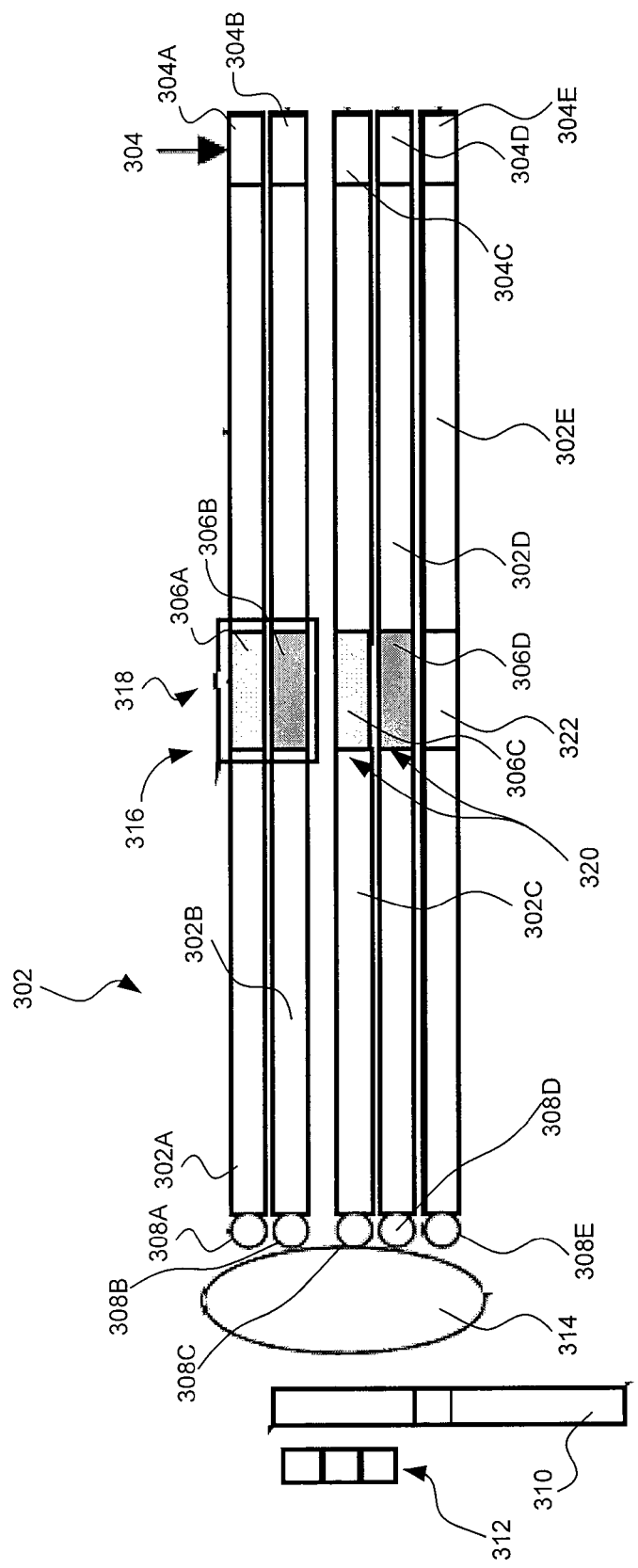
FIG. 3 shows an exemplary embodiment of a sensor of the present invention.

FIG. 3 illustrates one example of a sensor configuration according to the present invention. As shown in FIG. 3, the sensor configuration includes a plurality of light emitting diodes (LEDs) 312, and a bandpass filter 310 for filtering the light from the LEDs 312. A spherical collector lens 314 is used to collect the light and direct it to fibers 302. Optional ball lenses 308A-308E may be used to direct the light to fibers 302A-302E. Photodiodes 304 (which typically include matching photodiodes 304A-304E for each fiber 302A-302E) are located at the output end of the fibers 302, and are then used to measure outputs of the fibers 302.

It is to be appreciated that, as discussed below, an exemplary number of sample and reference fibers are shown, and that increasing the number of fibers will increase accuracy and resolution. However, a number of sample and reference fibers used is application specific.

Also shown in FIG. 3 is a sample area 316, which has an active area 306A of fiber 302A and an active area 306B of fiber 302B. Note that in this case fiber 302A is a sampling fiber, fiber 302B is a reference fiber and fiber 302B is also a sampling fiber. Fibers 302C and 302D are reference fibers, and fiber 302E is an uncoated reference fiber. Also shown in FIG. 3 are the active areas 306 each having a different coating, designated by 320, and including areas 306C and 306D. Separation of fibers 302 should preferably be minimized, but must be large enough to not allow light coupling between fibers 302.

The proposed sensor configuration improves sensor accuracy. The accuracy of the sensor configuration will be increased since the limited set of wavelengths produced by the LED source 312 and the one or more band-pass filters 310 will now be sampling M different fibers. For some of the M fibers, the peak may exist at the wavelength produced by a specific LED 312 and filter 310, for the others the peak will be between two adjacent wavelengths. A data reduction program can estimate the peak based on the average of the M calculated peaks by fitting a curve, such as a parabola, to the set of data points for all available wavelengths. A parabola can be fitted to each of the M data-sets and the M calibration parameters provide an n/wavelength shift for each. The effect is that the separate calibration parameters improve the resolution (and accuracy) of the sensor.

Figure 4:
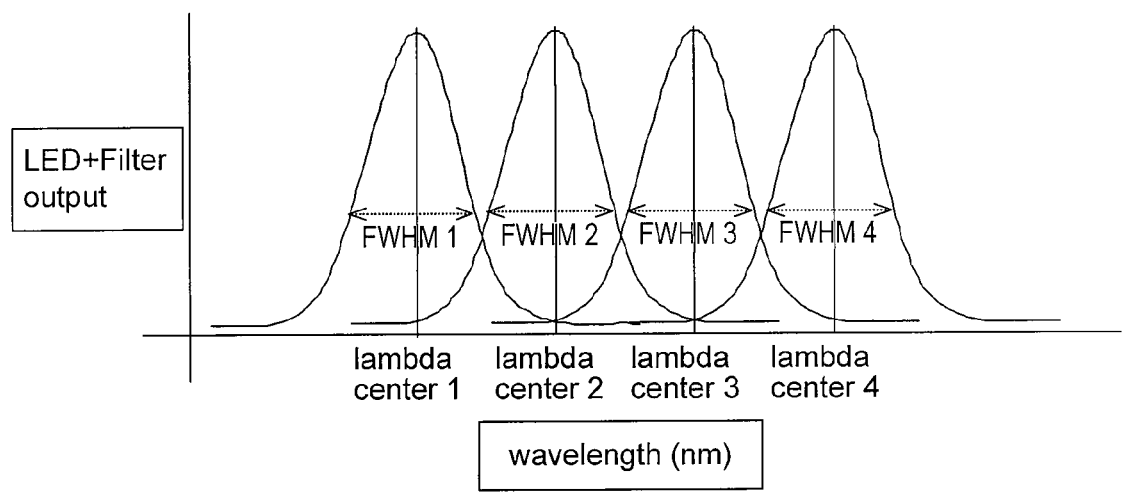
FIG. 4 shows a spectral throughput of a combination of several LEDs and fibers.

Typical fibers that may be used in the present invention are multi-mode fibers, with the active area of the sample and reference being in the central roughly 1 inch area of the fiber. Typical separation of the FWHM (full width half maximum) of the individual LED and filter combinations is on the order of 5-10 nm, as shown in FIG. 4.

The gold islands are usually ellipsoidal in shape (i.e., "flattened footballs"). The coating and annealing process will lead to a Gaussian distribution of the ratio R of the minor to major axis of the ellipsoid, centered about a particular center ratio $R_c$. R can be between 0.1 and 0.9 (depends on annealing temperature and time). The use of M fibers entails M different center ratios=$Rc_M$. A single island is roughly on the order of about 100 to 200 nm on the major axis. The number M can be at least 2, and usually greater than 2. Size of entire sensor increases with greater M.

Absorbance of the sample can be calculated as follows:

Absorbance from sample($A_s(\lambda)$)=−log('Sample' photodiode voltage($V_s(\lambda)$)/uncoated 'reference' photodiode voltage ($V_r(\lambda)$)).

Absorbance from reference($A_r(\lambda)$)=−log(coated 'reference' photodiode voltage($V_{cr}(\lambda)$)/uncoated 'reference' photodiode voltage($V_r(\lambda)$)).

Absorbance shift=($\lambda$ where $A_s(\lambda)$ is max)−($\lambda$ where $A_r(\lambda)$ is max).

Prior to unknown sample measurement, the sensor measures known refractive index liquids to obtain calibration parameter (n/$\lambda_{shift}$).

Index n of medium=Absorbance shift*calibration parameter.

The sensor should preferably be cleaned after every measurement.

Other than the custom coating and annealing of the sample and reference fibers, the components can be off the shelf, there are many commercial suppliers, such as Thorlabs, Inc. of Newton, N.J., USA, Newport Corporation of Irvine, Calif. USA, or Edmund Optics Inc., of Barrington, N.J.

It will be understood by those skilled in the art that various changes in form and details may be made therein without departing from the spirit and scope of the invention as defined in the appended claims. Thus, the breadth and scope of the present invention should not be limited by any of the above-described exemplary embodiments, but should be defined only in accordance with the following claims and their equivalents.

What is claimed is:

1. A system, comprising:
 a first reference fiber including first and second ends, the first end being configured to receive a beam of radiation and the second end capable of being spaced from a given sample;
 sensing fibers respectively coupled to plasmon sensors having corresponding various shapes, each of the sensing fibers is configured to receive the beam of radiation and is capable of being in contact with the sample;
 additional reference fibers, each of the additional reference fibers coupled to a plasmon sensor of a shape corresponding to a respective one of the sensing fibers, each of the additional reference fibers is configured to receive the beam of radiation, and is capable of being spaced from the sample;
 reference detectors configured to sense outputs from the first and the additional reference fibers; and
 sensing detectors configured to sense output from the sensing fibers.

2. The system of claim 1, wherein the sensing fibers are capable of being arranged in a planar array.

3. The system of claim 1, further comprising:
 an optical device configured to direct the beam of radiation into at least one of the first reference fiber, one or more of the sensing fibers, and one or more of the additional reference fibers.

4. The system of claim 3, wherein the optical device is a cylindrical lens.

5. The system of claim 3, wherein the optical device is a ball lens.

6. The system of claim 1, further comprising:
 a plurality of radiation sources that are configured to respectively direct corresponding beams of radiation into a corresponding one of the first reference fiber, the plurality of sensing fibers, and the additional reference fibers.

7. The system of claim 6, further comprising:
 one or more wavelength filters positioned between the source of radiation and the sensing fibers, wherein a wavelength of the beam of radiation entering one or more of the sensing fibers is selected using the one or more wavelength filters.

8. The system of claim 1, wherein the sensing fibers are capable of being arranged in a bundle as an array.

9. A method, comprising:
 directing light from an output of a first reference fiber onto a detector;
 directing light from outputs of a plurality of sensing fibers, each of the plurality of sensing fibers coupled to a plasmon sensor of a different shape, onto the detector;

directing light from outputs of additional reference fibers having plasmon sensors of shapes that correspond to the plasmon sensors of the respective sensing fibers onto the detector;

measuring, for each incident wavelength of light, a respective shift of resonant absorption peak wavelength associated with the outputs from respective pairs of the plurality of sensing fibers and its corresponding one of the additional reference fibers relative to the output from the first reference fiber for an index of refraction of a given sample of media during recirculation of the media; and calculating the index of refraction of a given sample of media based on the measured shifts of resonant absorption peak wavelengths for each of the incident wavelengths.

10. The method of claim 9, further comprising:

selecting a wavelength of light entering an input of the sensing fibers using wavelength filters.

11. The method of claim 9, further comprising:

focusing a light that is received at an input of the first reference fiber and the additional reference fibers using a ball lens.

12. The method of claim 9, further comprising:

focusing light that is received at an input of the sensing fibers using corresponding ball lenses.

13. The method of claim 9, further comprising:

focusing light from a plurality of light sources onto a cylindrical lens, the cylindrical lens focusing the light onto inputs of at least one of the first reference fiber, at least one of the additional reference fibers, and at least one of the plurality of sensing fibers.

14. The method of claim 9, further comprising:

using light emitting diodes as the plurality of light sources.

15. The method of claim 9, further comprising:

arranging the plurality of sensing fibers in a bundle.

* * * * *